United States Patent
Bessling et al.

(12)

(10) Patent No.: US 6,362,386 B1
(45) Date of Patent: Mar. 26, 2002

(54) METHOD AND DEVICE FOR OBTAINING ISOBUTENES FROM CONJUGATED HYDROCARBONS

(75) Inventors: Bernd Bessling, Grünstadt; Jean Werner Knab, Limburgerhof; Wolfgang Brox; Bernd Lohe, both of Heidelberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/446,532

(22) PCT Filed: Jul. 3, 1998

(86) PCT No.: PCT/EP98/04135
§ 371 Date: Dec. 28, 1999
§ 102(e) Date: Dec. 28, 1999

(87) PCT Pub. No.: WO99/01411
PCT Pub. Date: Jan. 14, 1999

(30) Foreign Application Priority Data

Jul. 4, 1997 (DE) .......................... 197 28 732

(51) Int. Cl.[7] ............................. C07C 7/00; C07C 7/148; C07C 41/00
(52) U.S. Cl. ...................... 585/800; 585/327; 585/639; 585/809; 568/697
(58) Field of Search ................................ 585/800, 809, 585/327, 639; 568/697

(56) References Cited

U.S. PATENT DOCUMENTS

| 4,242,530 A | | 12/1980 | Smith, Jr. ................... 585/510 |
| 4,287,379 A | | 9/1981 | Brunner et al. ............. 585/839 |
| 4,336,407 A | * | 6/1982 | Smith, Jr. ................... 568/697 |
| 4,395,580 A | * | 7/1983 | Juguin et al. ............... 585/639 |
| 4,409,421 A | * | 10/1983 | Herwig et al. .............. 585/833 |
| 4,447,668 A | * | 5/1984 | Smith, Jr. et al. ........... 585/639 |
| 4,448,643 A | | 5/1984 | Lindner et al. .............. 203/34 |
| 4,510,336 A | | 4/1985 | Hearn ....................... 568/697 |
| 4,847,431 A | * | 7/1989 | Nocca et al. ................ 568/197 |
| 5,368,691 A | * | 11/1994 | Asselineau et al. .......... 203/29 |
| 5,417,938 A | | 5/1995 | Shelden et al. ............. 422/196 |
| 5,567,860 A | * | 10/1996 | Mowry et al. .............. 585/639 |
| 5,684,213 A | | 11/1997 | Nemphos et al. ............ 568/698 |
| 5,994,594 A | * | 11/1999 | Marion et al. .............. 568/579 |
| 6,072,095 A | * | 6/2000 | Marion et al. .............. 585/639 |
| 6,100,438 A | * | 8/2000 | Marion et al. .............. 585/639 |
| 6,166,279 A | * | 12/2000 | Schwab et al. ............. 585/324 |

FOREIGN PATENT DOCUMENTS

| EP | 0 003 305 | 8/1979 |
| EP | 0 008 860 | 3/1980 |
| EP | 0 015 513 | 9/1980 |
| EP | 0 396 650 | 11/1990 |

* cited by examiner

Primary Examiner—Walter D. Griffin
(74) Attorney, Agent, or Firm—Keil & Weinkauf

(57) ABSTRACT

A process for isolating isobutene from a hydrocarbon mixture by a) combining the $C_4$-hydrocarbon mixture with a primary $C_3$- or $C_4$-alkanol;

b) reacting the isobutene in the $C_4$-hydrocarbon mixture with the primary $C_3$- or $C_4$-alkanol in the presence of a heterogeneous catalyst to give the corresponding tertiary ether of isobutene, c) separating the resultant reaction mixture into the relatively low-boiling, unetherified $C_4$-hydrocarbons and the relatively higher-boiling tertiary ether of isobutene with the aid of a distillation column, where the $C_4$-hydrocarbons are taken off at the top, and the tertiary ether of isobutene obtained at the bottom is transferred into a reactor, d) cleaving this ether into isobutene and the corresponding primary $C_3$- or $C_4$-alkanol, e) distilling this mixture from d) in a further distillation column, and taking off the isobutene as the top product, which comprises carrying out step a) in a zone (4C) containing reactive internals and containing the catalyst for carrying out step b) arranged in such a way that the zone (4C) is integrated into a distillation column (4), that a reactive distillation takes place in this zone (4C), and that the $C_3$- or $C_4$-alkanol is fed to the distillation column above the zone (4C) and the $C_4$-hydrocarbon mixture is fed to the distillation column below the zone (4C).

9 Claims, 1 Drawing Sheet

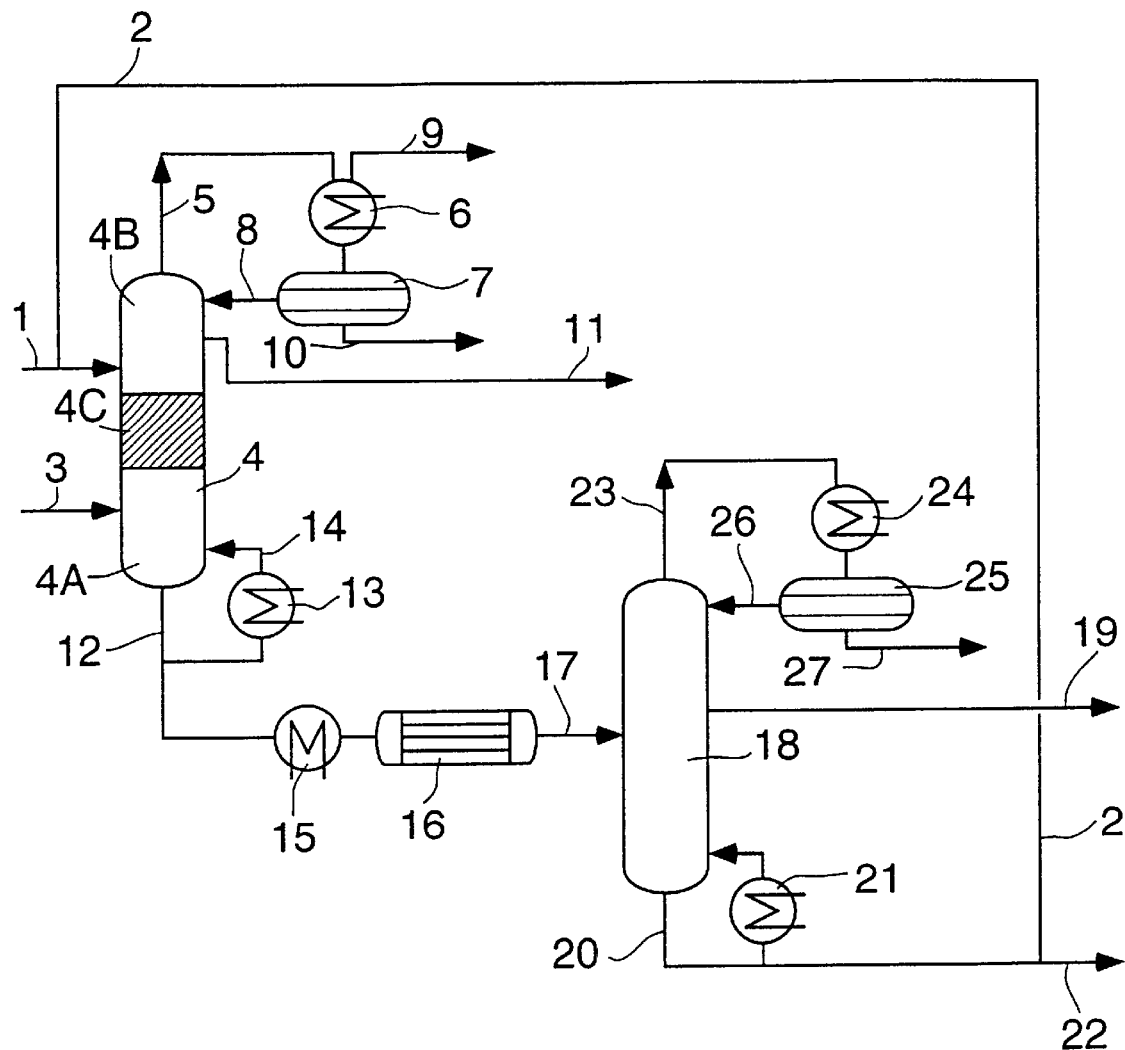

METHOD AND DEVICE FOR OBTAINING ISOBUTENES FROM CONJUGATED HYDROCARBONS

The invention relates to a process and apparatus for separating isobutene from $C_4$-hydrocarbon mixtures. The $C_4$-fraction used in this process, which has in most cases already been substantially freed from butadiene by extractive distillation, generally contains principally 1-butene, 2-butene (cis or trans) and n-butane in addition to isobutene. These $C_4$-hydrocarbon mixtures cannot be separated economically by simple fractional distillation owing to the inadequate boiling-point difference between its components. Higher-performance, more selective, physical and additionally also chemical separation processes are therefore used.

The latter are also used in particular for removing isobutene, since this differs from the remaining $C_4$-components through, inter alia, its higher reactivity. The chemical separation process on which the invention is based involves reaction of isobutene with a primary $C_3$- or $C_4$-alkanol in the presence of a catalyst to give the corresponding tertiary ether. After distillative separation thereof from the remainder of the $C_4$-hydrocarbon mixture followed by cleavage back into isobutene and the corresponding primary $C_3$- or $C_4$-alkanol, the isobutene is obtained as the top product after a further distillative separation step. At this point, some examples are defined which are used hereinafter:

The word "internals" is used as a general term for trays and packing. Such internals, which also enable the immobilization of heterogeneous catalysts (see, for example, EP-B1-0 396 650, EP-D1-0 008 860, are referred to more precisely below as reactive internals (reaction trays, reactive packing). Internals for exclusively distillative purposes are referred to as conventional.

In a known process for isolating isobutene from $C_4$-hydrocarbon mixtures, isobutene present therein is reacted with primary $C_3$- or $C_4$-alkanol to give the corresponding tertiary ether (EP-E-0 015 513 and EP-B-0 003 305). The reaction is catalyzed by ion exchanger resins. In order to achieve an adequate conversion, the reaction is carried out in a cascade of three reactors, between which cooling is effected. In the first reactor, kinetic aspects mean that the etherification is carried out at a higher temperature than in the second and third reactors, in which the temperature is set so that it has a favorable effect on the chemical equilibrium of the exothermic etherification. In order to achieve satisfactory conversions, it is also necessary to use a significant excess of primary alkanol. If isobutanol is used, the molar starting ratio between the latter and isobutene is approximately 1.7:1 (ether formed: isobutyl tert-butyl ether (IBTBE)). The corresponding tertiary ether is then separated from the remainder of the $C_4$-hydrocarbon mixture in a distillation column. After thermal, catalytic cleavage of the ether, isobutene is obtained as the top product in a further distillation.

It is an object of the present invention to improve the processes described above for isolating isobutene from $C_4$-hydrocarbon mixtures so that
1. the complexity of the apparatus is reduced, and
2. higher conversions are achieved, so that the molar starting ratio between the primary $C_3$- or $C_4$-alkanol and isobutene can be reduced.

We have found that this object is achieved by a process for isolating isobutene from a hydrocarbon mixture by
 a) combining the $C_4$-hydrocarbon mixture with a primary $C_3$- or $C_4$-alkanol;
 b) reacting the isobutene in the $C_4$-hydrocarbon mixture with the primary $C_3$- or $C_4$-alkanol in the presence of a heterogeneous catalyst to give the corresponding tertiary ether of isobutene,
 c) separating the resultant reaction mixture into the relatively low-boiling, unetherified $C_4$-hydrocarbons and the relatively higher-boiling tertiary ether of isobutene with the aid of a distillation column, where the $C_4$-hydrocarbons are taken off at the top, and the tertiary ether of isobutene obtained at the bottom is transferred into a reactor,
 d) cleaving the ether into isobutene and the corresponding primary $C_3$- or $C_4$-alkanol,
 e) distilling this mixture from d) in a further distillation column, and taking off the isobutene as the top product.

The novel process comprises carrying out step a) in a zone containing reactive internals and containing the catalyst for carrying out step b) arranged in such a way that the zone is integrated into a distillation column, that a reactive distillation takes place in this zone, and that the $C_3$- or $C_4$-alkanol is fed to the distillation column above the zone and the $C_4$-hydrocarbon mixture is fed to the distillation column below the zone.

The invention also provides an apparatus for carrying out the abovementioned process, which apparatus has the following devices:
 i) a distillation column containing reactive and conventional internals
 ii) two phase separators,
 iii) a catalyst bed,
 iv) a distillation column, and
 v) connecting lines between devices i) to iv).

The inventive idea of being able to carry out the basic chemical separation process with the aid of a reactive distillation is based on the knowledge that a reaction (isobutene reacted with a primary alkanol) and a distillation can be carried out under the same conditions. The prerequisite is that the product has a higher boiling point than the starting materials, that the starting materials have different boiling points (prerequisite for countercurrent flow of the starting materials), and that the boiling point difference between the two starting materials is not excessive (adequate residence time of the starting materials is necessary in the zone in which the reaction takes place). In addition, it must be possible to carry out the reaction with high conversion under the distillation conditions, the selectivity must be high, and the corresponding etherification must be reversible.

In the present process, a more precise term for the zone as etherification location would be reactive distillation zone. This is arranged in the central part of the distillation column and, in accordance with the invention, contains reactive internals, with pure distillations taking place in the regions above and below this zone. For these regions, conventional internals are provided. The reactive internals can be a catalyst on the corresponding residence-time trays or in their outflow or, in the case of packing, included therein in the manner of a pocket. Packing elements can be correspondingly coated. The catalyst used can be suitable known catalysts. These include, for example, ion exchanger resins in the [$H^+$] form (Bayer Levatit®). Depending on the thermal stability of the catalysts, the reaction temperature and consequently the pressure can vary. The corresponding increase in reaction rate allows a more compact design of the column. The temperatures should be selected so that the catalyst is not damaged. At the same time, it is desirable to keep the condensation temperatures significantly above ambient temperature. The correlations between concentration, pressure and temperature for a given system are known per se.

For the isobutene/primary $C_3$- or $C_4$-alkanol/relevant tertiary ether system, a temperature damage limit for the catalyst of, for example, 150° C. thus gives a possible pressure range of from 3 to 8 bar and temperatures of from 25 to 190° C. in the interior of the column. A pressure of about 5 bar is preferred. The temperature in the reactive distillation zone of the column is then from 35° C. to 190° C., preferably from 50° C. to 160° C. Higher temperatures may not only be damaging to the catalyst, but also favor side-reactions, for example elimination of water from the alkanol, oligomerization of isobutene or etherification of two alkanols.

The dependence of the reaction rate on the system temperature determines the requisite catalyst volume. An essential advantage of the reactive distillation described, owing to the countercurrent flow of the starting materials, is the high etherification conversion caused by the more favorable location of the chemical equilibrium. For the same molar starting ratio between the primary alcohol and isobutene, higher conversions are achieved than in the process described by EP-B-0 015 513 or EP-B-0 003 305 (cascade of three reactors). On the other hand, the high conversion allows the molar starting ratio between the primary alcohol and isobutene to be significantly reduced. For the process described, the latter is preferably 1.1:1. A lower alkanol content in the reactive distillation zone reduces the amount of "residual alkanol" to be removed from the still. This is associated firstly with a reduction in the circulation streams and secondly the chemical equilibrium of the ether cleavage is favorably affected. Owing to the high conversions, the process described is particularly suitable in etherification for the preparation of $C_4$-hydrocarbon mixtures having a particularly low isobutene content (isobutene is harmful to certain processes). For this purpose, a higher starting material content of the primary alcohol is advantageously selected. The molar starting ratio between the primary alcohol and isobutene is generally from about 1.7:1 to 1.0:1.

Owing to the reduction in the apparatus complexity, achieved according to the invention by the integration of the reaction zone (in EP-B-0 015 513 and EP-B-0 003 305, a cascade of three reactors for the etherification) into the distillation column, not only are material costs reduced in plant construction, but the energy necessary for the process is also reduced. The heat of reaction from the exothermic etherification is advantageously also utilized directly for the distillation.

Further details and advantages of the invention are given in the following description of the illustrative embodiment of the novel process shown diagrammatically in the drawing.

Here, the upper part of a distillation column is fed with fresh isobutanol through a line 1 and with recycled isobutanol through a line 2. Separately, the lower part of the distillation column 4 is fed with a $C_4$-hydrocarbon mixture through a line 3. The isobutene-containing $C_4$-hydrocarbon mixture fed through line 3 can originate, for example, from the thermal cracking of petroleum products, in which case it contains isobutane, n-butane, 1-butene, trans-2-butene, cis-2-butene and residual butadiene in addition to isobutene. The distillation column 4 is provided, for example, with internals arranged one above the other, forming three separate zones. The lower zone containing conventional internals 4A forms a stripping section. The upper zone containing conventional internals 4B forms a rectifying section. The central zone containing reactive internals 4C is a reactive distillation section. The reactive packing in this zone 4C is provided with a heterogeneous catalyst. The $C_4$ gas mixture fed through line 3 is introduced below this zone 4C, while the isobutanol is introduced through line 1 above this zone 4C.

Separate introduction of the two starting materials produces countercurrent flow. In the rectifying section 4B, the low-volatility isobutanol is separated from the remainder of the $C_4$ mixture. In the stripping section 4A, the IBTBE is separated from an isobutanol azeotrope and isolated as bottom product. The countercurrent flow of the starting materials and the distillative removal of the products from zone 4C enables high conversions. Only a small amount of isobutanol leaves column 4. The starting ratio between isobutanol and isobutene is generally 1.1:1.

An isobutene-free $C_4$-fraction is taken off from the top of the column 4 through line 5 and condensed in the heat exchanger 6. The condensates are then fed to the phase separator 7. The organic phase formed therein, essentially consisting of $C_4$-fraction, is fed back to the top of column 4 through line 8. Any residual moisture can then be removed as aqueous phase through line 10. Offgas is removed from the upper part of the heat exchanger 6 through line 9. Raffinate II, which no longer contains isobutene, is removed through line 11. This gas mixture can be converted into, for example, octenes, nonanol or plasticizers in subsequent process steps.

The IBTBE formed is taken off from the stripping section 4A of the distillation column 4 through line 12, and some thereof is heated in a heat exchanger 13 and fed back to the bottom of column 4 through line 14. The IBTBE obtained is then cleaved in the conventional manner and worked up by distillation. The isobutanol is recycled to the etherification column. This is carried out in the manner described below.

The IBTBE obtained is heated in a heat exchanger 15 to the temperature necessary for the subsequent reaction and fed to a catalyst bed 16, in which the IBTBE is cleaved into isobutene and isobutanol and fed to the distillation column 18 through line 17. In this column 18, which is provided with conventional internals, the target product isobutene is separated off by distillation. Pure isobutene is taken off through line 19. The bottom product from column 18, which essentially consists of isobutanol and unreacted IBTBE, leaves the column through line 20. Some thereof is recycled into column 18 after heating by heat exchanger 21. The majority of this isobutanol is recycled to column 4 through line 2. A small amount is removed through line 22 for purging of high-boiling impurities. The gas mixture taken off from the top of column 18 through line 23 is condensed in heat exchanger 24 and separated in the subsequent phase separator into a condensate comprising hydrocarbons, which is recycled into column 18 through line 26, and water, which is removed through line 27.

The etherification of isobutene using isobutanol by the novel reactive distillation is described below with reference to an example.

Laboratory column 4 consists, for example, of a column having a diameter of 0.055 m. The rectifying section 4B and the stripping section 4A (lower reaction zone) were each formed by two conventional elements of structured packing (300 $m^2/m^3$) of 1 m. The reactive section 4C was formed by reactive packing provided with an ion exchanger resin (tradename Lewatit 2631 from Bayer), separated into four build-in elements of 1 m, each with collectors and distributors. Catalyst content was about 30% by vol.

The feed of 2.5 kg/h of isobutanol was above zone 4C, and the raffinate I was introduced below zone 4C in an amount of 6.5 kg/h containing 25% by weight of isobutene. IBTBE was taken off as bottom product in liquid form through line 12.

The unreacted low-boiling components ($C_4$) were condensed and taken off as distillate, with a reflux ratio of about 2.

The operating pressure was 5 bar in order to facilitate condensation temperatures above room temperature. The temperatures at the reactive internals were insufficient to cause damage to the catalyst. At a pressure of 5 bar, the bottom and top temperatures were set at 165 and 47° C. respectively. The temperatures in the reaction section and the distillative rectifying section (approximately 65° C.) were determined by the $C_4$-components.

More than 97% of the isobutene was reacted with isobutanol.

In a typical experiment, an isobutanol:isobutene molar ratio of 1.1 was used. This is significantly below the value of 1.7 in the conventional, sequential reactor column arrangement.

The top product did not contain any measurable amounts of isobutanol or IBTBE and contained <1.5% by weight of isobutene. The bottom product contained traces of isobutene (0.3% by weight), the excess butanol (about 10% by weight) and 1% by weight of other butyl ethers in addition to IBTBE. About 50% by weight of IBTBE and 5% by weight of isobutanol were present directly beneath the reactive distillation zone.

We claim:

1. A process for isolating isobutene from a $C_4$-hydrocarbon mixture consisting essentially of 1-butene, cis 2-butene, trans 2-butene, n-butane and isobutene by a) combining said $C_4$-hydrocarbon mixture with a primary $C_3$- or $C_4$-alkanol, b) reacting the isobutene in said $C_4$-hydrocarbon mixture with said primary $C_3$- or $C_4$-alkanol in the presence of a heterogeneous catalyst to give the corresponding tertiary ether of isobutene, c) separating the resultant reaction mixture into the relatively low-boiling, unetherified $C_4$-hydrocarbons and the relatively higher-boiling tertiary ether of isobutene with the aid of a distillation column, where the $C_4$-hydrocarbons are taken off at the top, and the tertiary ether of isobutene obtained at the bottom is transferred into a reactor, d) cleaving this ether into isobutene and the corresponding primary $C_3$- or $C_4$-alkanol, e) distilling this mixture from d) in a further distillation column, and taking off the isobutene as the top product, which comprises carrying out step a) in a zone containing reactive internals and containing the catalyst for carrying out step b) arranged in such a way that said zone is integrated into a distillation column, that a reactive distillation takes place in said zone, and that said $C_3$- or $C_4$-alkanol is fed separately to the distillation column above said zone and said $C_4$-hydrocarbon mixture is fed separately to the distillation column below said zone so that there is countercurrent flow of said alkanol and said hydrocarbon mixture.

2. A process as claimed in claim 1, wherein the molar starting ratio between the alkanol and isobutene is from 1.7:1 to 1.0:1.

3. A process as claimed in claim 1, wherein the temperature in said zone is from 35° C. to 190° C.

4. A process as claimed in claim 1, wherein the pressure in said zone is from 3 to 6 bar.

5. A process as claimed in claim 1, wherein the primary alkanol employed is isobutanol.

6. A process as claimed in claim 1, wherein the heterogeneous catalyst employed is an ion exchanger.

7. A process as claimed in claim 2, wherein said molar starting ratio is 1.1:1.

8. A process as claimed in claim 3, wherein said temperature is from 50° C. to 160° C.

9. A process as claimed in claim 4, wherein said pressure is about 5 bar.

* * * * *